(12) United States Patent
Stewart et al.

(10) Patent No.: US 6,755,790 B2
(45) Date of Patent: Jun. 29, 2004

(54) TRANSSEPTAL ACCESS TISSUE THICKNESS SENSING DILATOR DEVICES AND METHODS FOR FABRICATING AND USING SAME

(75) Inventors: Mark T. Stewart, Lino Lakes, MN (US); Harry A. Puryear, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 51 days.

(21) Appl. No.: 10/269,768

(22) Filed: Oct. 14, 2002

(65) Prior Publication Data

US 2004/0073110 A1 Apr. 15, 2004

(51) Int. Cl.⁷ .................................................. A61B 8/14
(52) U.S. Cl. ...................................................... 600/466
(58) Field of Search ................................ 600/407–471, 600/508; 607/99–101, 122; 606/37–40; 73/625, 626; 128/898, 916

(56) References Cited

U.S. PATENT DOCUMENTS

| | | | |
|---|---|---|---|
| 3,971,363 A | * 7/1976 | Fletcher et al. ............. | 600/508 |
| 5,220,924 A | 6/1993 | Frazin ..................... | 128/662.06 |
| 5,385,148 A | 1/1995 | Lesh et al. .............. | 128/662.06 |
| 5,617,584 A | 4/1997 | Brennan ........................ | 2/206 |
| 5,803,083 A | 9/1998 | Buck et al. ............ | 128/660.03 |
| 5,873,855 A | 2/1999 | Eggers et al. | |
| 6,024,703 A | 2/2000 | Zanelli et al. .............. | 600/437 |
| 6,246,158 B1 | 6/2001 | Ladabaum ................... | 310/334 |
| 6,325,797 B1 | 12/2001 | Stewart et al. ................ | 606/41 |

\* cited by examiner

*Primary Examiner*—Ali M. Iman
(74) *Attorney, Agent, or Firm*—Paul H. McDowall; Girma Wolde-Michael (57) ABSTRACT

The present invention relates to medical devices; in particular, the present invention provides devices and methods for sensing thickness of cardiac tissue and the like so that medical procedures may be efficiently performed through and/or upon a discrete location having suitable tissue thickness. The invention includes an elongated resilient dilator apparatus having an ultrasound transceiver coupled thereto. When the ultrasound transceiver is disposed proximate a region of relatively thin tissue, such as a latent Fossa Ovalis valve, a clinician receives a signal. The clinician may then proceed with enhanced confidence to pierce the relatively thin tissue. Thus, in the case of a transseptal procedure, the clinician gains access to the left atrial chamber from the right atrial chamber.

16 Claims, 7 Drawing Sheets

TRANSSEPTAL ACCESS TISSUE THICKNESS SENSING DILATOR DEVICES AND METHODS FOR FABRICATING AND USING SAME

FIELD OF THE INVENTION

The present invention relates to medical devices; in particular, the present invention provides devices and methods for sensing thickness of cardiac tissue and the like so that medical procedures may be efficiently performed through and/or upon a discrete location having suitable tissue thickness.

BACKGROUND OF THE INVENTION

The present invention relates to dilation and/or ablation catheters for treatment of cardiac arrhythmia, for example atrial fibrillation. More particularly, it relates to a catheter configured for transseptal access to the left atrium so that a mapping and/or ablation catheter can be advanced into the left atrium. As is known in the art, an ablation catheter is used to electrically isolate a vessel, such as a pulmonary vein, from a chamber, such as the left atrium with a continuous lesion pattern and a method for forming such a lesion pattern.

The heart includes a number of pathways that are responsible for the propagation of signals necessary to produce continuous, synchronized contractions. Each contraction cycle begins in the right atrium where a sinoatral node initiates an electrical impulse. This impulse then spreads across the right atrium to the left atrium, stimulating the atria to contract. The chain reaction continues from the atria to the ventricles by passing through a pathway known as the atrioventricular (AV) node or junction, which acts as an electrical gateway to the ventricles. The AV junction delivers the signal to the ventricles while also slowing it, so the atria can relax before the ventricles contract.

Disturbances in the heart's electrical system may lead to various rhythmic problems that can cause the heart to beat irregularly, too fast or too slow. Irregular heart beats, or arrhythmia, are caused by physiological or pathological disturbances in the discharge of electrical impulses from the sinoatrial node, in the transmission of the signal through the heart tissue, or spontaneous, unexpected electrical signals generated within the heart. One type of arrhythmia is tachycardia, which is an abnormal rapidity of heart action. There are several different forms of atrial tachycardia, including atrial fibrillation and atrial flutter. With atrial fibrillation, instead of a single beat, numerous electrical impulses are generated by depolarizing tissue at one or more locations in the atria (or possibly other locations). These unexpected electrical impulses produce irregular, often rapid depolarizations in the atrial muscles. These impulses can conduct to the ventricles causing potentially lethal ventricular arrhythmias. Patients experiencing atrial fibrillation may suffer from fatigue, activity intolerance, dizziness and even strokes.

The precise cause of atrial fibrillation, and in particular the depolarizing tissue causing "extra" electrical signals, is currently unknown. As to the location of the depolarizing tissue, it is generally agreed that the undesired electrical impulses often originate in the left atrial region of the heart. Recent studies have expanded upon this general understanding, suggesting that nearly 90% of these "focal triggers" or electrical impulses are generated in one (or more) of the four pulmonary veins (PV) extending from the left atrium.

It has been postulated that this tissue may spontaneously depolarize, resulting in an unexpected electrical impulse(s) propagating into the left atrium and along the various electrical pathways of the heart. In this regard, as the heart develops from an embryotic stage, left atrium tissue may grow or extend a short distance into one or more of the PVs. In addition, during gestation an intra-atrial valve (i.e., the Fossa Ovalis valve) remains open and closes, or is rendered latent, following birth. The latent valve provides a relatively thin tissue location through which a catheter may advance for access to the left atrium. Unfortunately, the latent valve is difficult to locate using traditional means such as fluoroscopy.

A variety of different atrial fibrillation treatment techniques are available, including drugs, surgery, implants, and catheter ablation. While drugs may be the treatment of choice for some patients, drugs typically only mask the symptoms and do not cure the underlying cause. Implantable devices, on the other hand, usually correct an arrhythmia only after it occurs. Surgical and catheter-based treatments, in contrast, will actually cure the problem by ablating the abnormal tissue or accessory pathway responsible for the atrial fibrillation thereby disrupting ionic conduction pathways of the abnormal tissue. The catheter-based treatments rely on the application of various destructive energy sources to the target tissue, including direct current electrical energy, radio frequency (RF) electrical energy, laser energy, and the like. The energy source, such as an ablating electrode, is normally disposed along a distal portion of a catheter.

Most ablation catheter techniques employed to treat atrial fibrillation focus upon locating the ablating electrode, or a series of ablating electrodes, along extended target sections of the left atrium wall. Because the atrium wall, and thus the targeted site(s), is relatively tortuous, the resulting catheter design includes multiple curves, bends, extensions, etc. In response to recent studies indicating that the unexpected electrical impulses are generated within a PV, efforts have been made to ablate tissue within the PV itself. Obviously, the prior catheter designs incorporating convoluted, multiple bends are not conducive to placement within a PV. Instead, a conventional "straight ended" ablation catheter has been employed. While this technique of tissue ablation directly within a PV has been performed with relatively high success, other concerns may arise.

More particularly, due to the relatively small thickness of atrial tissue formed within a PV, it is likely that ablation of this tissue may in fact cause the PV to shrink or constrict. Because PV's have a relatively small diameter, a stenosis may result. Even further, other vital bodily structures are directly adjacent each PV. These structures may be undesirably damaged when ablating within a PV.

In light of the above, an alternative technique has been patented by Medtronic, Inc. whereby a continuous ablation lesion pattern is formed in the left atrium wall about the ostium associated with the PV in question. In other words, the PV is electrically isolated from the left atrium by forming an ablation lesion pattern that surrounds the PV ostium. As a result, any undesired electrical impulse generated within the PV could not propagate into the left atrium, thereby eliminating unexpected atria contraction. One exemplary patent related to the foregoing is U.S. Pat. No. 6,325,797 the contents of which are hereby incorporated by reference herein.

Unfortunately, while PV isolation via a continuous ablation lesion pattern about the PV ostium appears highly viable, no acceptable ablation catheter configuration exists.

Most atrial fibrillation ablation catheters have linear distal ends, designed for manipulation in a sliding fashion along the atrial wall. That is to say, the distal, electrode-carrying end of the catheter is typically slid along (or parallel to) the atrial wall. With this generally accepted configuration in mind, it may be possible to shape the distal, electrode-carrying end into a small ring sized in accordance with the PV ostium. For example, U.S. Pat. No. 5,617,854 discloses one such possibility. More particularly, the described ablation catheter includes a substantially ring-shaped portion sized to contact the ostium of the coronary sinus. Pursuant to conventional designs, the ring extends linearly from the catheter body. In theory, the ringshaped portion may be placed about a PV ostium. However, proper positioning would be extremely difficult and time consuming. More particularly, it would be virtually impossible to locate and then align the ring about a PV ostium when sliding the catheter along the atrium wall. The ring must be directed toward the ostium in a radial direction (relative to a central axis of the ostium). Even if the electrophysiologist were able to direct the ring to the ostium, the periodic blood flow through the PV would likely force the ring away from the atrium wall, as the catheter body would not provide any support.

A related concern entails mapping of a PV prior to ablation. In cases of atrial fibrillation, it is necessary to identify the origination point of the undesired electrical impulses prior to ablation. Thus, it must first be determined if the electrical impulse originates within one or more PVs. Once the depolarizing tissue has been identified, necessary ablation steps can be taken. Mapping is normally accomplished by placing one or more mapping electrodes into contact with the tissue in question. In order to map tissue within a PV, therefore, a relatively straight catheter section maintaining two or more mapping electrodes must be extended axially within the PV. Ablation catheters configured to slide along the atrial wall cannot include a separate, distal extension for placement within the PV. Instead, an entirely separate mapping catheter must be provided and then removed for subsequent replacement with the ablation catheter. Obviously, these additional steps greatly increase the overall time required to complete the procedure.

Electrical isolation of a pulmonary vein via an ablation lesion pattern surrounding the pulmonary vein ostium presents a potentially revolutionary technique for treatment of atrial fibrillation. However, the unique anatomical characteristics of a pulmonary vein and left atrium render currently available ablation catheters minimally useful. Therefore, a substantial need exists for an ablation catheter designed for rapid and accurate identification of the latent Fossa Ovalis valve so that a suitable catheter may be advanced therethrough.

SUMMARY OF THE INVENTION

The present invention provides an improved apparatus for performing a septal puncture procedure and methods for fabricating and using same. In one form of the invention, a remotely deployable thickness sensing probe couples to a distal end of an elongated cardiac tissue dilator or cardiac tissue ablation apparatus and provides a signal related to relative tissue thickness adjacent the probe. The dilator or ablation apparatus is preferably resilient to axial compression and torque. To efficiently fabricate such apparatus low cost, non-imaging thickness sensing probes are preferred. Such probes may be electrically wired or may provide signals wirelessly to remote (i.e., external) medical monitoring equipment. The thickness sensing probe may comprise acoustic-type sensor probes (e.g., so-called ultrasound-, ultrasonic-types). Such probes transmit and receive (i.e., transceive) signals that penetrate a local region of tissue. The signals relate to the volume of tissue proximate the probe. The signals may be used to confirm location of a relatively thin portion of tissue suitable for temporarily being pierced during a medical procedure such as a cardiac procedure requiring transseptal access. While a unitary transceiver is desirable, separate transmitting and receiving units may be used.

In addition to the foregoing, the signals provided according to the present invention may also be used to determine how much ablation energy (e.g., radio frequency, laser, etc.) or where a surgical ablation apparatus should be applied to a surface, such an endocardial surface.

In practice, an apparatus according to the present invention is used to interrogate a tissue surface and provide signals relating to the thickness of a local region of the tissue. This information is then conveyed to a clinician. The information can be displayed on a monitor or other remote device, can be conveyed as an acoustic signal (e.g., varying pitch, tone or volume based on a sensed thickness parameter of tissue), and/or can be conveyed as a tactile response, and the like. A variety of tissue thicknesses may be interrogated; however, for the transseptal tissue of interest, a range of about 0.1 mm to approximately 10 mm is preferred. The magnitude and frequency of acoustic energy delivered the transducer should of course be designed as appropriate for a given tissue region.

With respect to axial compression and torque ranges for the elongated portion of the apparatus, a design similar to those current tissue dilators having a Brockenbrough needle coupled thereto is generally suitable for use in conjunction with the present invention. A marking or identification unit is preferably disposed on or near the distal end portion of the apparatus so that the orientation and location of the end portion may be viewed (e.g., using a fluoroscope and the like).

The region of tissue preferably comprises a latent Fossa Ovalis valve of a patient for a transseptal procedure. In such a procedure, a clinician advances the distal end of a catheter to the right atrium, and then probes for an appropriate region of reduced thickness to pierce to gain access to the left atrium. Since most humans have such a latent valve structure left over from gestation, this is a preferred route for accessing the left atrium so that left atrial chamber and the pulmonary valves therein may be accessed so that a variety of therapies may be applied thereto.

DETAILED DESCRIPTION OF THE ILLUSTRATED EMBODIMENTS

Figure 1:
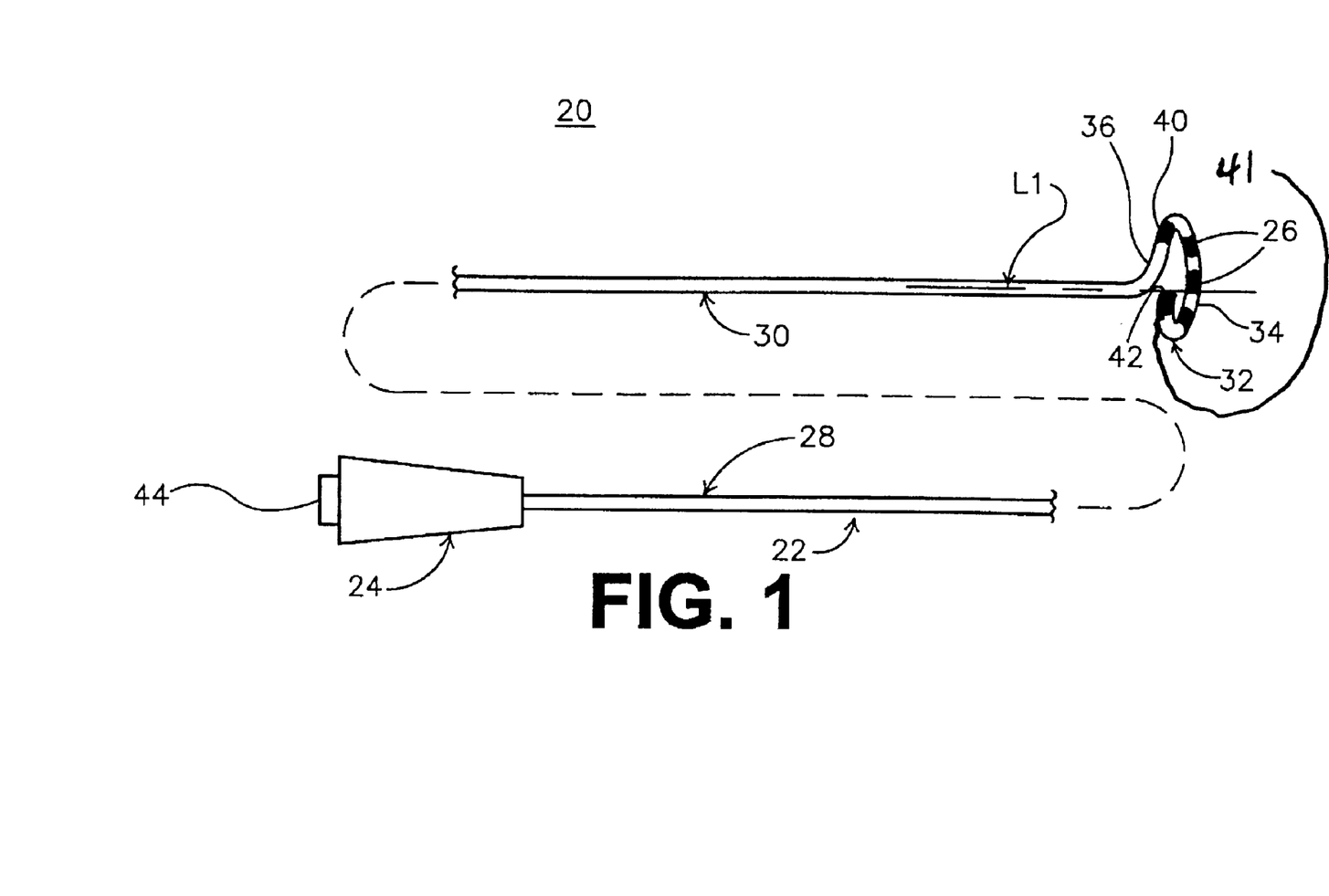
FIG. 1 is a side-elevational view of a catheter assembly in accordance with the present invention.

One preferred embodiment of a catheter assembly 20 in accordance with the present invention is shown in FIG. 1. The catheter assembly 20 is comprised of a catheter body 22, a handle 24 and electrodes 26. As described in greater detail below, the catheter body 22 extends from the handle 24, and the electrodes 26 arc disposed along a portion of the catheter body 22. While various configurations of the distal portion of the catheter body 22 are depicted herein, a linear, curvilinear or complex distal portion may be employed according to the present invention. Furthermore, while not depicted in the drawings the distal portion may be manipulated (e.g., using interior pull-wires, shape memory alloys, and the like) to form advantageous configurations for a given medical procedure. In addition, the catheter body 22 may include a lumen for fluid delivery at or near the distal end. As is known in the art, such fluid delivery may include isotonic saline solution to form so-called virtual electrode regions, marker dye or other material that is advantageously dispensed in, on or near a cardiac tissue location.

The catheter body 22 is defined by a proximal portion 28, an intermediate portion 30 and a distal portion 32, and includes a central lumen (not shown). Although not specifically shown, the catheter body may be configured for over-the-wire or rapid exchange applications. In one preferred embodiment, the proximal portion 28, the intermediate 30 and the distal portion 32 are integrally formed from a biocompatible material having requisite strength and flexibility for deployment within a heart. Appropriate materials are well known in the art and include polyamide.

The intermediate portion 30 extends from the proximal portion 28. The proximal portion 28 and the intermediate portion 30 are preferably flexible, so as to facilitate desired articulation during use. In general terms, however, the intermediate portion 30 defines a longitudinal axis L1. It should be recognized that in one position, the longitudinal axis L1 extends linearly through the intermediate portion 30 and the proximal portion 28. Upon deployment, it may be that the proximal portion 28 and/or the intermediate portion 30 is forced to a curved or curvilinear orientation. With this in mind, the longitudinal axis L1 is more specifically defined as a center of the intermediate portion 30 adjacent a point of intersection between the distal portion 32 and the intermediate portion 30.

The distal portion 32 extends from the intermediate portion 30 and forms a loop 34. In one preferred embodiment, the loop 34 is circular, formed in a plane transverse to the longitudinal axis L1. To this end, the distal portion 32 preferably includes a lateral segment 36. The lateral segment 36 extends in a generally lateral fashion from the intermediate portion 30. The loop 34 extends from the lateral segment 36 in an arcuate fashion, turning or revolving about a central loop axis. While the loop 34 is shown in FIG. 1 as forming a single revolution about the central loop axis, the loop 34 may instead include a plurality of revolutions to define a spiral or coil. In the one preferred embodiment depicted in FIG. 1, the central loop axis is aligned with the longitudinal axis L1. Alternatively, however, the lateral segment 36 may be eliminated such that the loop 34 extends directly from the intermediate portion 30. Even further, the lateral segment 36 may be configured such that the central loop axis is offset from the longitudinal axis L1. Regardless of the exact construction, however, the central loop axis is preferably substantially parallel to the longitudinal axis L1.

Regardless of the exact shape, the loop 34 preferably defines an enclosed area greater than a size of an ostium (not shown) associated with a particular vessel to be isolated, as described in greater detail below. In one preferred embodiment, the catheter assembly 20 is configured to electrically isolate a pulmonary vein from the left atrium. With this one preferred application, where the loop 34 is circular, the loop 34 has a diameter in the range of approximately 10–20 mm, more preferably 15 mm, although other sizes, either greater or smaller, are acceptable.

The loop 34 may be formed in a variety of ways, such as by incorporating a preformed section of super elastic, shape memory material, such as Nitinol, with a loop configuration. To facilitate guiding of the distal portion 32 into a heart (not shown), the catheter assembly 20 may include a stylet (not shown) internally disposed within the catheter body 22. In an extended position, the stylet would extend through the distal portion 32, so as to render the loop 34 straight. Upon retraction of the stylet, the distal portion 32 would form the loop 34. Alternatively, the catheter assembly 20 may include a sheath (not shown) slidably receiving the catheter body 22. Prior to deployment, the distal portion 32 would be retracted within the sheath, rendering the loop 34 straight. Upon deployment from the sheath, the distal portion 32 would form the loop 34. Other similar approaches for providing the loop 34 are similarly acceptable.

The handle 24 is preferably sized to be grasped by a user and includes an electrical connector 44. The electrical connector provides electrical connections to the electrodes 26 carried by the distal portion 32. To this end, wire(s) (not shown) may extend within the central lumen (not shown) from the distal portion 32 to the handle 24.

Figure 4A:
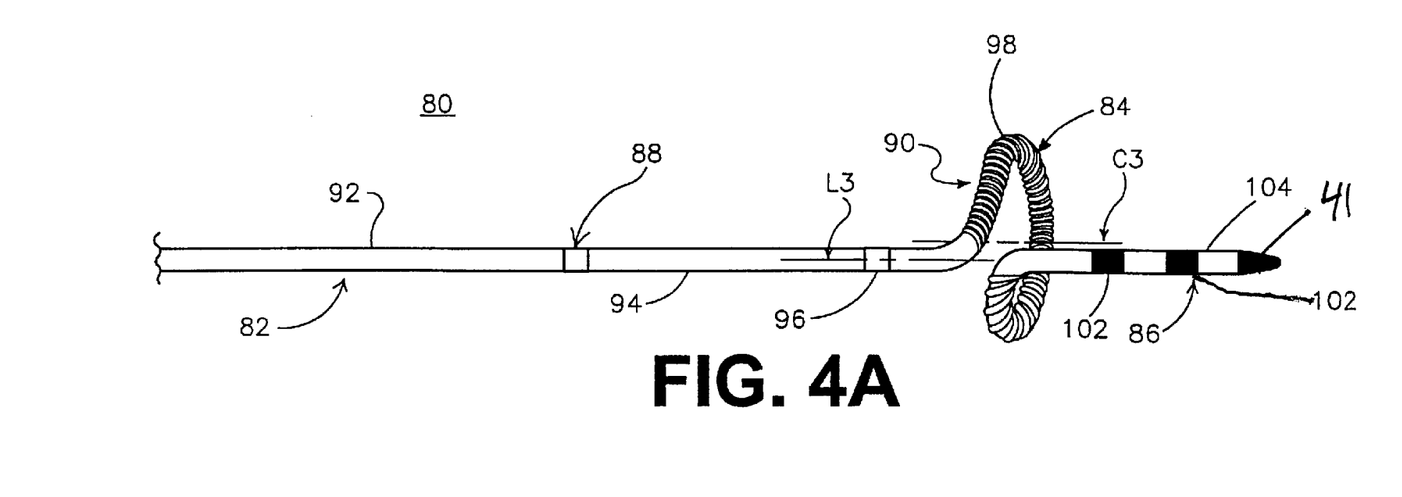
FIG. 4A is a perspective view of a portion of an alternative catheter assembly in accordance with the present invention.
Figure 5:
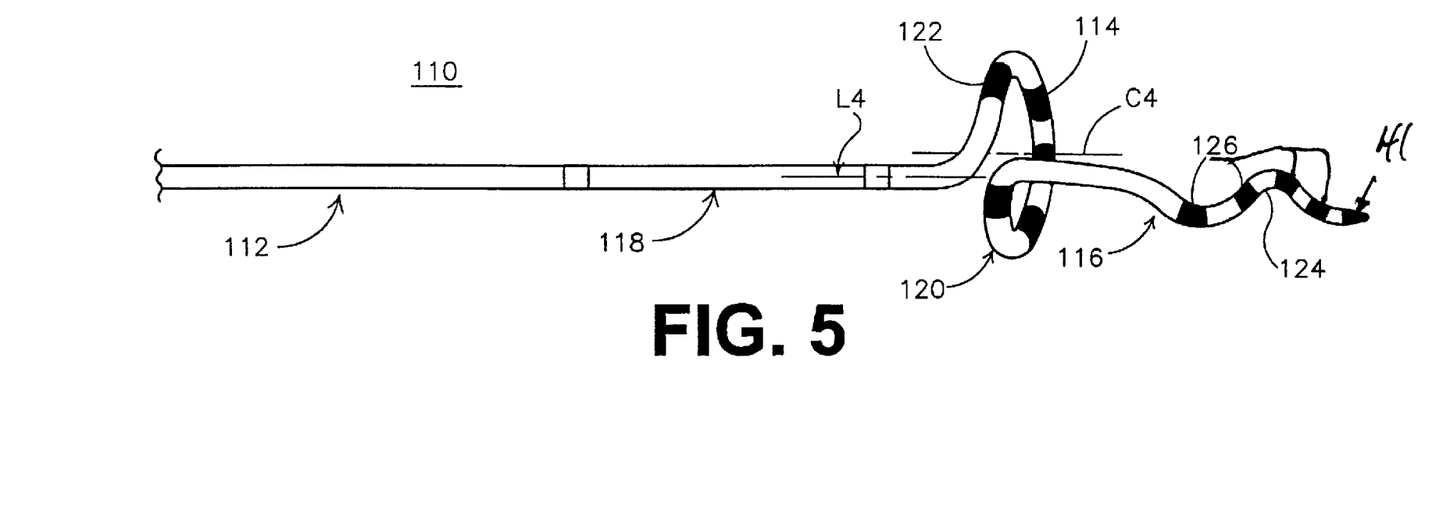
FIG. 5 is a perspective view of one embodiment of a portion of a catheter constructed according to the present invention.

The electrodes 26 are preferably of a type known in the art and are preferably a series of separate band electrodes spaced along the loop 34. Instead of, or in addition to, separate band electrodes, the electrodes 26 may include one or more spiral or coil electrodes, or one or more counter-electrodes. Additionally, the electrodes 26 are preferably non-thrombogenic, non-coagulum or char forming. The electrodes 26 may be cooled by a separate source (not shown), such as a saline source. The electrodes 26 may be electrically isolated from one another, or some or all of the electrodes 26 may be electrically connected to one another. Preferably, however, at least one electrode 26 is provided. The electrodes 26 are preferably shaped and positioned such that during an ablation procedure, a continuous, closed therapeutically-effective lesion pattern is created. Preferably, the length of each of the electrodes 26 is about 4–12 mm, more preferably about 7 mm. The spacing between each of the electrodes 26 is preferably about 1–3 mm, and more preferably about 2 mm. Finally, to effectuate a continuous, closed lesion pattern, preferably one of the electrodes 26 is disposed at the proximal end 40 of the loop 34, and a tissue thickness sensing probe unit 41 is disposed at the distal end 42. The probe unit 41 preferably comprises a low cost ultrasound transducer capable of reliably measuring tissue thickness of about 0.1 mm and approximately 10 mm. The probe unit 41 preferably does not include ultrasound imaging circuitry and is coupled to remote tissue monitoring circuitry (not shown) such an RF energy generator and/or mapping system. Such a system preferably provides a visual, tactile or aural indication when the probe unit 41 is disposed adjacent a relatively thin region of cardiac tissue. The cardiac tissue is preferably a latent Fossa Ovalis valve. As previously described, it is not necessary that the loop segment 38 be formed such that the proximal end 40 and the distal end 42 are integral or that the distal end forms part of the radius of the loop segment 38. Indeed, the distal end 42 and the probe unit 41 are preferably more or less parallel to longitudinal axis L1 (as depicted in FIG. 4A and FIG. 5). With this in mind, the spacing or gap between the electrode 26 at the proximal 40 and the electrode 26 at the distal end 42 is preferably less than about 5 mm.

A The probe unit 41 may comprise any commercially available transceiver capable of providing at least a rudimentary signal related to tissue thickness proximate the probe unit 41. Some representative ultrasonic probe units 41 such as those patented previously in the U.S. include those disclosed in the following patents: U.S. Pat. No. 6,246,158 issued to Ladabaum; U.S. Pat. No. 6,024,703 issued to Zanelli et al.; U.S. Pat. No. 5,803,083 issued to Buck et al.; U.S. Pat. No. 5,385,148 issued to Lesh et al.; and U.S. Pat. No. 5,220,924 issued to Franzin. The contents of the foregoing patents are hereby incorporated by reference as if fully set forth herein.

Figure 2A:
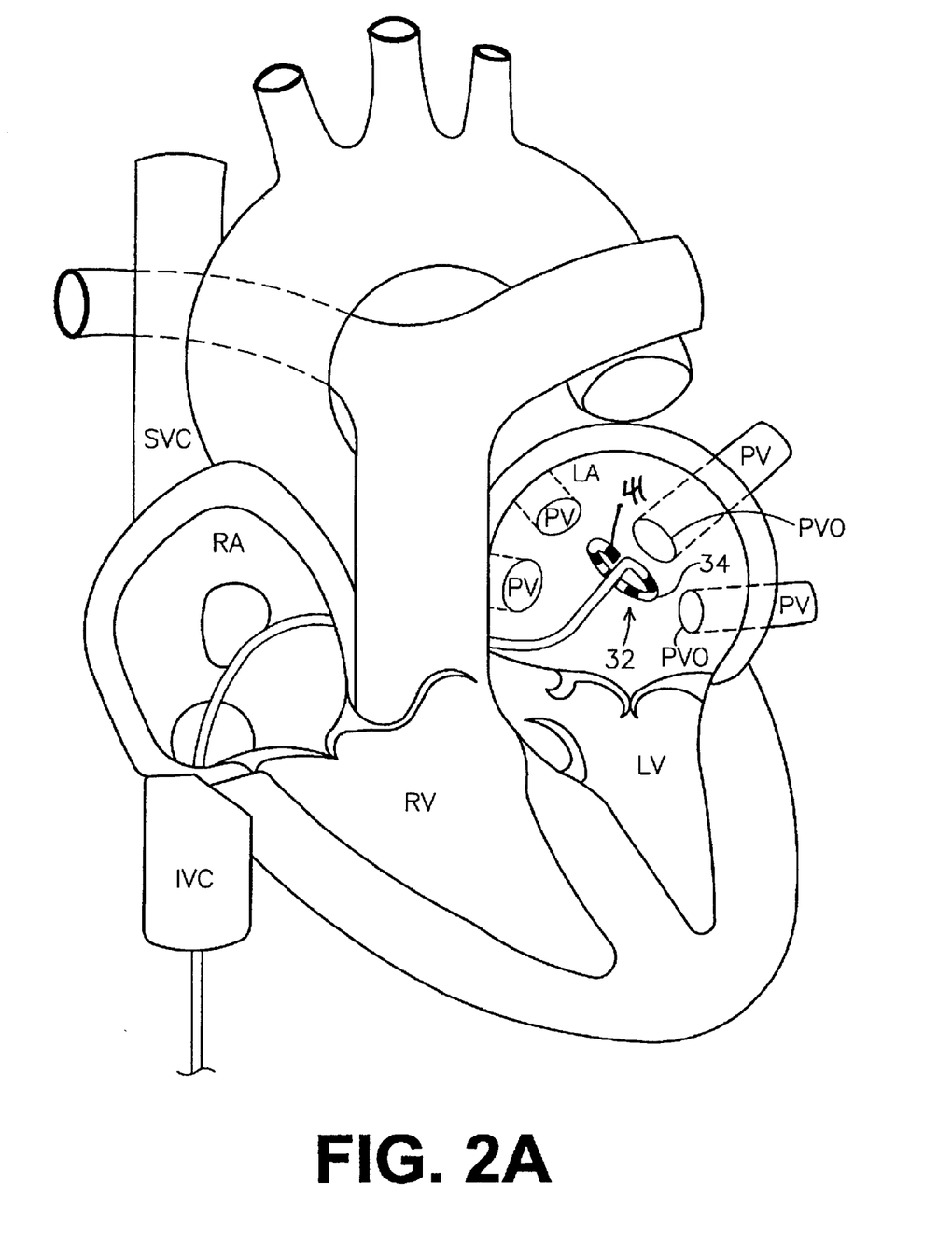
FIGS. 2A–2B illustrates use of the catheter assembly of FIG. 1 within a heart.
Figure 2B:
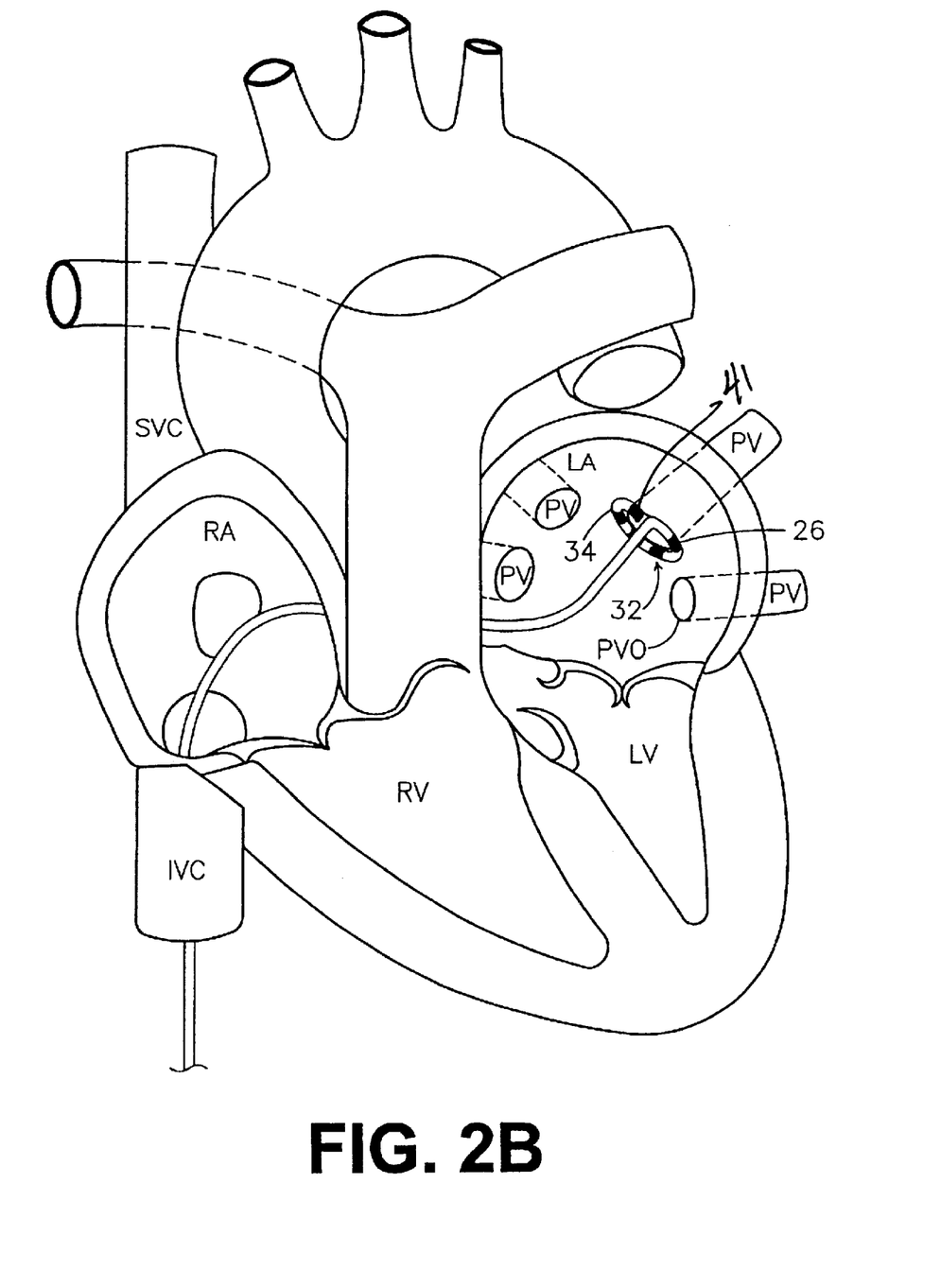
Figure 3:
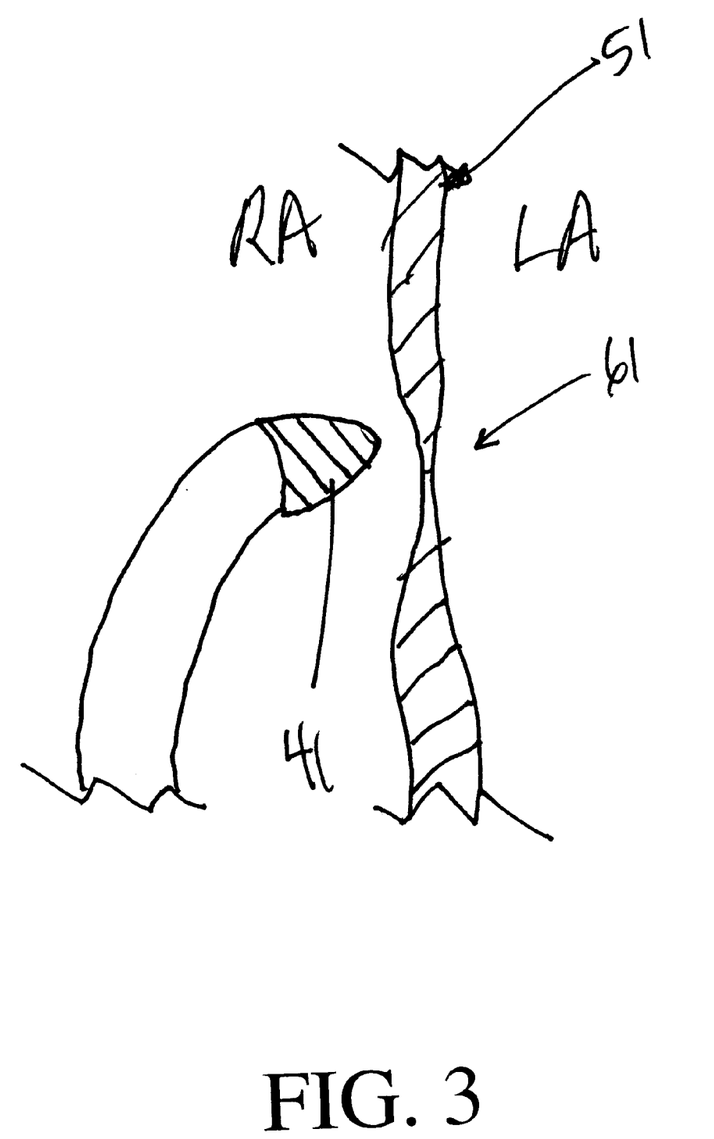
FIG. 3 is a side view of a portion of an alternative catheter assembly in accordance with the present invention.

FIGS. 2A and 2B illustrate use of the catheter assembly 20 shown in FIG. 1 within a heart 50. As a point of reference, the heart 50 includes a right atrium (RA), a left atrium (LA), a right ventricle (RV) and a left ventricle (LV). An inferior vena cava (IVC) and a superior vena cava (SVC) lead into the RA. The RA is separated from the LA by an interarterial septum 51 (shown in cross section in FIG. 3) typically having a latent Fossa Ovalis valve formed therethrough (generally indicated by arrow 61). This latent valve 61 provides an appropriate site to introduce a medical instrument such as a mapping and/or ablation catheter to provide diagnosis and therapy to portions of the LA, respectively. Finally, four pulmonary veins PV extend from the left atrium LA. Each of the pulmonary veins PV forms an ostium PVO in the left atrium LA wall. As previously described, during formation of the heart 50, it is possible that tissue of the left atrium LA may grow upwardly into one or more of the pulmonary veins PV. This left atrium LA tissue may spontaneously depolarize, resulting in atrial fibrillation. Notably, the heart 50 may be formed such that a separate ostium PVO is not formed for each individual pulmonary vein PV. In other words, a single pulmonary vein ostium PVO may be formed for two pulmonary veins PV. For example, a single pulmonary vein ostium PVO may be formed for both the left inferior pulmonary vein PV and the left superior pulmonary vein PV, with the two pulmonary veins PV bifurcating from the single ostium PVO.

As shown in FIG. 2A, electrical isolation of a pulmonary vein PV begins by directing the distal portion 32 of the catheter body 22 through the inferior vena cava IVC, into the right atrium RA through a puncture in the interarterial septum preferably located at the site of a latent Fossa Ovalis valve (as suggested in FIG. 3) and into the left atrium LA. In practice, a clinician advances the catheter body 22 into the RA and then switches on (or begins monitoring) the probe unit 41 and begins interrogating the tissue of the septal wall. When the probe unit 41 indicates that a tissue region or tissue location of reduced thickness is proximate the probe unit 41, an aural, tactile and/or visual signal alerts the clinician to stop interrogating. The clinician may optionally confirm (or reconfirm) that the probe unit 41 (and catheter body 22) are in fact aligned or oriented appropriately prior to piercing the septal wall. The optional step may involve fluoroscopy with or without dispensing marker material in or near the region of reduced thickness identified by the probe unit 41. In one embodiment of the present invention, a single electrical conductor switcheably couples a remote tissue monitoring system to either the electrodes 26 or the probe unit 41.

Alternatively, the introduction of the distal portion 32 of the catheter body 22 into the right atrium RA is also suggested by passage of the distal portion 32 into the right atrium RA through the superior vena cava SVC. The loop 34 is positioned slightly spaced from the ostium PVO associated with the pulmonary vein PV to be treated. More particularly, the loop 34 is positioned such that the central loop axis is approximately aligned with a center of the pulmonary vein ostium PVO. The catheter body 22 is then advanced distally such that the loop 34 contacts the left atrium LA wall about the pulmonary vein ostium PVO in question, as shown in FIG. 2B. In other words, the catheter body 22 is advanced in a direction parallel with the central loop axis such that the loop 34 contacts the left atrium LA wall, surrounding the pulmonary vein ostium PVO. Importantly, because the central loop axis is parallel to the longitudinal axis L1, the catheter body 22 longitudinally supports advancement of the loop 34. In other words, the longitudinal axis L1 is effectively aligned with the pulmonary vein ostium PVO such that blood flow from the pulmonary vein PV acts along the longitudinal axis L1. Thus, the catheter body 22 limits deflection of the loop 34 otherwise caused by blood flow from the pulmonary vein PV.

The electrodes 26 (shown in FIG. 1) are then energized to a sufficient level to ablate the contacted tissue, for example with an RF source. In one preferred embodiment, the electrodes 26 ablate the left atrium LA tissue for 30–120 seconds at a temperature in the range of approximately 60–70 degree C. As a result, a continuous, closed lesion pattern is formed around the pulmonary vein ostium PVO. Pursuant to the above described catheter assembly 20 configuration, the lesion pattern is formed in a plane substantially perpendicular to the longitudinal axis L1. Notably, while the lesion pattern is shown as being only slightly larger than the pulmonary vein ostium PVO, the loop 34 (FIG. 1) may be sized to produce an even larger ablation lesion pattern. To this end, where a single pulmonary vein ostium PVO is formed for two pulmonary veins PV, the resulting pulmonary vein ostium PVO may be elongated. As shown in FIG. 2B, then, the loop 34 (FIG. 1) is configured to form a continuous, closed lesion pattern about the elongated-shaped pulmonary vein ostium PVO.

The continuous, closed lesion pattern electrically isolates the pulmonary vein PV from the left atrium LA. Any undesired electrical impulses generated in the pulmonary vein are effectively "stopped" at the lesion pattern, and will not propagate into the left atrium LA.

An alternative embodiment of a catheter assembly 80 is shown in FIG. 4A. The catheter assembly 80 includes a catheter body 82, an electrode 84, a locating device 86 and a tissue thickness sensing probe unit 41. For ease of illustration, only a portion of the catheter assembly 80 is shown, and catheter assembly 80 may further include a handle similar to the handle 24 associated with the catheter assembly 20 (FIG. 1) previously described. Also, the electrode 84 and the probe unit 41 are electrically coupled to a remote tissue monitoring system as previously described and, in general, as known in the art.

Catheter body 82 is defined by a proximal portion (not shown), an intermediate portion 88 and a distal portion 90. The intermediate portion 88 extends from the proximal portion and is defined by a proximal segment 92 and a distal segment 94. In a preferred embodiment, the distal segment 94 is preferably more flexible than the proximal segment 92. With this configuration, the distal segment 94 can more easily deflect relative to the proximal segment 92, thereby facilitating desired positioning of the distal portion 90 during deployment. In this regard, an internal pull wire (not shown) may be provided to effectuate desired deflection of the distal segment 94. Even further, an anchor 96 is preferably included for facilitating a more radical displacement of the distal portion 90 relative to the intermediate portion 88.

As with previous embodiments, the intermediate portion 88 defines a longitudinal axis L3. Once again, where the intermediate portion 88 is axially aligned with the proximal portion (not shown), the longitudinal axis L3 is linear along the intermediate portion 88 and the proximal portion. However, because the intermediate portion 88 is preferably bendable relative to the proximal portion, and further because the distal segment 94 may bend relative to the proximal segment 92, the longitudinal axis L3 is more succinctly defined by the intermediate portion 88 at the point of intersection between the intermediate portion 88 and the distal portion 90.

Similar to the catheter assembly 20 (FIG. 1) previously described, the distal portion 90 preferably forms a loop 98. The loop 98 may include one or more loop segments (one is shown in FIG. 4A), with each loop segment revolving around a central loop axis C3. The loop 98 is formed substantially transverse to the longitudinal axis L3, with the central loop axis C3 preferably aligned with the longitudinal axis L3. Alternatively, the central loop axis C3 may be slightly offset from the longitudinal axis L3. Regardless, the central loop axis C3 is preferably parallel with the longitudinal axis L3.

The electrode 84 is shown in FIG. 4 as being a continuous coil electrode. Alternatively, a plurality of spaced, band electrodes or counter-electrodes may be used.

Figure 4B:
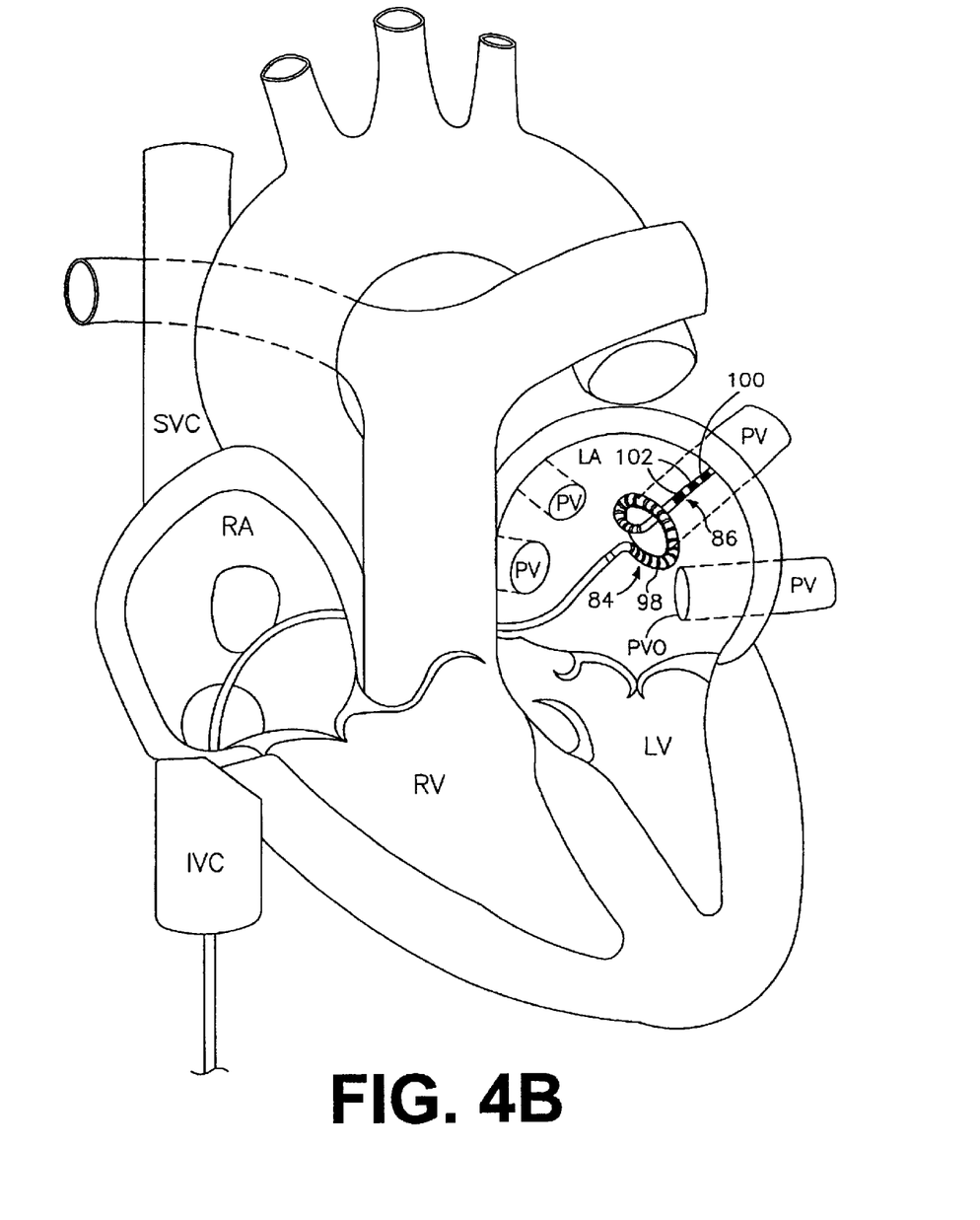
FIG. 4B illustrates placement of the catheter assembly of FIG. 4A within the left atrium of a heart.

Finally, the locating device 86 includes a tip portion 104 configured to extend distal the loop 98. In one preferred embodiment, the locating device 86 is integrally formed with the catheter body 82, extending from the distal portion 90. Alternatively, the locating device 86 may be a separate body. Regardless, the tip portion 104 extends distal the distal portion 90, and is generally aligned with the central loop axis C3 defined by the loop 98. The tip portion 104 preferably has a diameter less than a diameter of a pulmonary vein, and a length in the range of approximately 1–15 mm. Further, as shown in FIG. 4A, the tip 104 may include a series of mapping electrodes 102 and a probe unit 41. The mapping electrodes 102 are electrically connected to an external recording system (not shown) for providing information indicative of tissue polarization and the probe unit 41 is electrically connected to circuitry which provides an indication of relative tissue depth proximate the probe unit 41, as previously described herein. A common electrical conductor may be used to couple the electrodes 102 and the probe unit 41 that is separately addressable (e.g., employs an electronic switch, different multiplex circuitry, and/or other addressing techniques known in the art). Preferably, the As shown in FIG. 4B, during use, the catheter assembly 80 is directed into the left atrium LA as previously described. The locating device 86, and in particular the tip 100, is then used to locate the pulmonary vein ostium PVO. Once located, the tip 100 is inserted into the pulmonary vein PV, effectively centering the loop 98 around the pulmonary vein ostium PVO. Where the tip 100 includes the mapping electrodes 102, a mapping procedure can be performed, whereby information indicative of tissue activity nearby the mapping electrodes 102 is provided. During this mapping procedure, a determination can be made as to whether the particular pulmonary vein PV is generating undesired electrical impulses. Where it is determined that, in fact, tissue in the pulmonary vein PV is spontaneously depolarizing, the electrode 84 is energized to form the continuous, closed lesion pattern about the pulmonary vein ostium PVO as previously described.

Yet another alternative embodiment of a catheter assembly 110 in accordance with the present invention is shown in FIG. 5. The catheter assembly 110 is highly similar to the catheter assembly 80 (FIG. 4A) and includes a catheter body 112, electrodes 114 and a locating device 116. The catheter body 112 includes a proximal portion (not shown) an intermediate portion 88 defining a longitudinal axis L4 and a distal portion 120. The distal portion 120 extends from the intermediate portion 118 and forms a loop 122 substantially transverse to the longitudinal axis L4. In this regard, the loop 122 revolves about a central loop axis C4. In one preferred embodiment, the central loop axis C4 is aligned with the longitudinal axis L4. Alternatively, the central loop axis C4 is offset from, but substantially parallel with, the longitudinal axis L4. The electrodes 114 (shown as spaced band electrodes) are disposed along the loop 122 for forming a continues, closed lesion pattern.

The locating device 116 includes a tip 124 that extends distal the loop 122. In one preferred embodiment, the locating device 116 is integrally formed with the catheter body 112 and includes mapping electrodes 126 connected to an external recording device (not shown). Alternatively, the locating device 116 may be a separate body. As shown in FIG. 5, the tip 124 forms a descending diameter coil, generally aligned with the central loop axis C4. By providing a coil configuration for the tip 124, the tip 124 facilitates a more positive centering of the loop 122 about a pulmonary vein ostium PVO (FIG. 4B). In one preferred embodiment, the tip 124 defines a maximum diameter approximating a diameter of a pulmonary vein. When inserted within a pulmonary vein, then, the tip 124 effectively lodges along the pulmonary vein wall. This, in turn, positions the loop 122 in a more central fashion about the associated ostium. Further, by providing the mapping electrodes 126, the locating device 116 additionally serves as a mapping device for evaluating a particular pulmonary vein.

Figure 6:
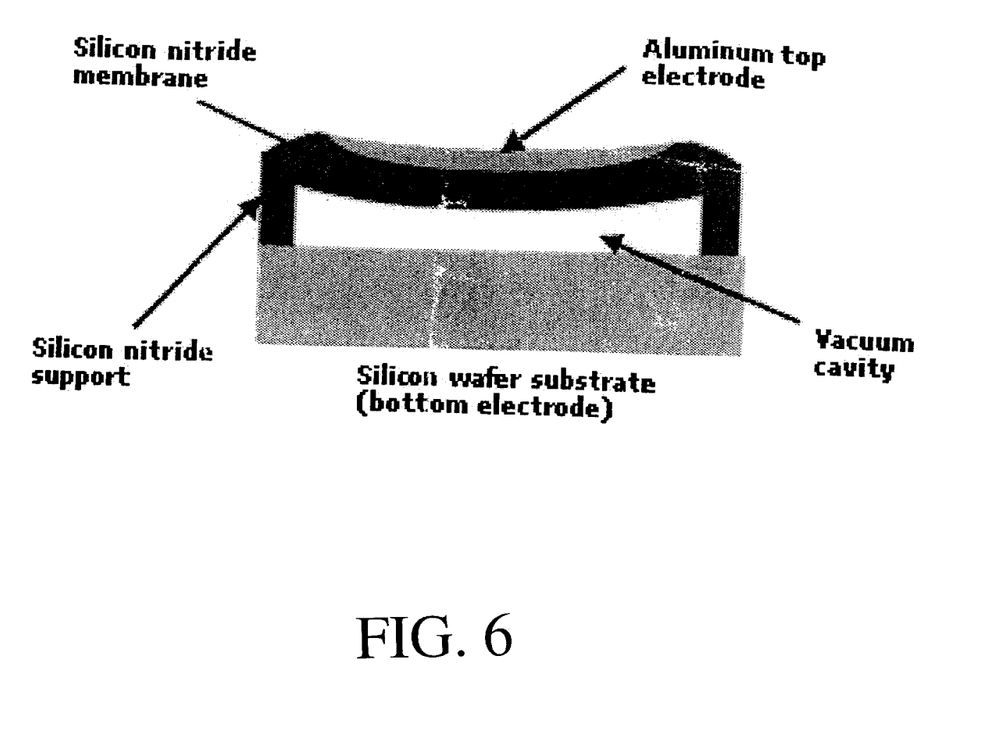
FIG. 6 is an elevational side view in cross section depicting an exemplary ultrasound transducer that may be used in conjunction with the present invention.

A preferred sensor structure forming a part of the probe unit 41 is depicted in FIG. 6. This particular structure is provided by Sensant Corporation of San Jose, Calif. Fundamentally, these sensor devices are capacitive structures. A DC bias voltage is applied across the top and bottom electrodes establishing an electric field that creates tension in the suspended membrane. An AC signal voltage applied across the membrane varies this tension and causes it to vibrate, emitting ultrasonic waves. Conversely, during reception of ultrasound echoes, an acoustic wave impinges on the top membrane causing it to move. The changing distance between the top and bottom plates of the capacitor produce variations in capacitance that result in an output voltage signal. For air or gas applications, the sensor operates in a resonant mode to maximize its sensitivity. However, in immersion or water applications, the sensors are extremely broadband for optimal pulse-echo signal quality and broadband frequency response. The sensor utilized for use in the probe unit 41 may produce a wireless signal indicative of a region of tissue having reduced thickness.

Although the present invention has been described with reference to preferred embodiments, workers skilled in the art will recognize that changes may be made in form and detail without departing from the spirit and scope of the invention. For example, the preferred embodiment has described electrical isolation of a pulmonary vein from the left atrium for treatment of atrial fibrillation. Alternatively, the method and apparatus of the present invention may be utilized in the treatment of other cardiac arrhythmias, such as isolating the coronary sinus from the left atrium or isolating the outflow tract (or pulmonary valve) from the right ventricle. Further, a number of the described embodiments have included a catheter body forming a single loop. Alternatively, a multi-plane coil or spiral may be formed. The coil or spiral may increase or decrease in diameter as it extends distally, or may have a uniform diameter. Additionally, while the loop has been described as preferably being circular, a variety of other substantially closed shapes, including square, triangular, octagonal, etc. are equally acceptable. Also, several of the described embodiments have included a locating device for centering the loop about a pulmonary vein ostium and for mapping a pulmonary vein. In this regard, the locating device may be configured to serve only as a centering device or only as a mapping device, or both. Finally, other features may be incorporated into the catheter assembly. For example, to expedite deployment, the catheter assembly may be configured to slidably receive a guide wire used to position the catheter assembly within the left atrium. Even further, the catheter assembly may include a rapid exchange feature for quick placement over and removal from the guide wire.

We claim:

1. An elongated medical apparatus for tranvenously locating a relatively thin, mechanically pierceable region of tissue, comprising:
 a resilient elongated body unit having a proximal end and a distal end wherein at least one orientation marker is coupled to a portion of the body unit said resilient elongated body unit adapted for transvenous deployment to a portion of endocardium;
 a non-imaging volume thickness sensor coupled to a portion of the distal end and providing signals related to a thickness dimension of an adjacent region of endocardial tissue without first piercing said endocardial tissue; and
 a means for conveying the signals to a clinician.

2. A medical apparatus according to claim 1, further comprising at least one electrode coupled to a portion of the distal end.

3. A medical apparatus according to claim 2, wherein the at least one electrode is a tissue mapping electrode.

4. A medical apparatus according to claim 2, wherein the volume thickness sensor comprises an ultrasonic transceiver, wherein said ultrasonic transceiver is not adapted for providing a signal encoding a visual image of the adjacent region of endocardial tissue, and wherein a distal portion of the resilient elongated body unit comprises at least one compressible loop portion disposed substantially orthogonal to a longitudinal axis of said resilient elongated body unit.

5. A medical apparatus according to claim 2, wherein the adjacent region of tissue comprises a portion of a latent Fossa Ovalis valve.

6. A medical apparatus according to claim 1, wherein the means for conveying comprises a wireless telemetry system.

7. A medical apparatus according to claim 6, further comprising an antenna coupled to the sensor for conveying the signals and wherein an elongated electrical conductor provides electrical energy to power the volume thickness sensor.

8. A method of fabricating an elongated medical apparatus for transvenously locating a relatively thin, mechanically pierceable region of tissue, comprising:
 coupling a thickness sensor to a distal end portion of an electrified elongated resilient member, wherein said thickness sensor provides an output signal without piercing a portion of tissue and is not adapted for providing a signal encoding a visual image of an adjacent region of tissue;
 electrically coupling the thickness sensor to an electrical conductor disposed within the electrified !elongated resilient member, wherein said electrical conductor is the only electrical conductor disposed within said electrified elongated resilient members and
 forming at least one compressible loop disposed in a distal portion, and substantially orthogonal to a major longitudinal axis, of said electrified elongated resilient member.

9. A methods according to claim 8, further comprising at least one orientation marker coupled to the electrified elongated resilient member.

10. A method according to claim 9, further comprising:
 sharpening a portion of the distal end of the electrified elongated resilient member disposed adjacent the sensor.

11. A method according to claim 10, wherein said sharpened portion extends helically a from the distal end portion.

12. A method according to claim 11, wherein at least one electrode is disposed adjacent the sharpened portion and further comprising:
 coupling a switching for selectively providing electrical communication between the at least one electrode or the thickness sensor and a remote tissue monitoring device.

13. A method according to claim 12, wherein the thickness sensor comprises an ultrasound transducer, wherein said ultrasound transducer is not adapted for providing a signal encoding a visual image of the adjacent region of tissue.

14. A method according to claim 13, wherein the ultrasound transducer provides a wireless signal related to the depth of tissue adjacent an end portion of the transducer to the remote tissue monitoring device.

15. A method of using an elongated medical apparatus to transvenously locate and subsequently pierce a region of tissue having a reduced thickness dimension, such as a latent Fossa Ovalis valve, comprising:
 interrogating a region of septal tissue with an ultrasound transceiver disposed near a distal end of a tissue dilator apparatus, wherein said ultrasound transceiver is not adapted for providing a signal encoding a visual image of the adjacent region of tissue;
 providing an aural, a tactile or a simple visual signal to a clinician, wherein said signal relates to a thickness dimension of the region of septal tissue; and
 advancing the distal end of the tissue dilator apparatus when the signal indicates a region of reduced thickness of said septal tissue so that said distal end pierces said region of reduced thickness.

16. A method according to claim 15, further comprising at least one electrode disposed on the tissue dilator apparatus and further comprising the step of:
 switching an electrical contact between said ultrasound transceiver and the at least one electrode and a remote tissue monitoring apparatus so that said clinician can either receive the signal or receive an electrical communication from the at least one electrode.

* * * * *

UNITED STATES PATENT AND TRADEMARK OFFICE
CERTIFICATE OF CORRECTION

PATENT NO. : 6,755,790 B2  
DATED : June 29, 2004  
INVENTOR(S) : Stewart et al.

It is certified that error appears in the above-identified patent and that said Letters Patent is hereby corrected as shown below:

Column 12,
Line 28, replace "a switching for" with -- a switch for --.

Signed and Sealed this

Fifteenth Day of March, 2005

JON W. DUDAS
*Director of the United States Patent and Trademark Office*